US009339634B2

(12) United States Patent
Cox (10) Patent No.: US 9,339,634 B2
(45) Date of Patent: May 17, 2016

(54) LOCAL DELIVERY WITH A BALLOON COVERED BY A CAGE

(71) Applicant: Daniel L. Cox, Palo Alto, CA (US)

(72) Inventor: Daniel L. Cox, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 72 days.

(21) Appl. No.: 13/762,011

(22) Filed: Feb. 7, 2013

(65) Prior Publication Data

US 2013/0218077 A1  Aug. 22, 2013

Related U.S. Application Data

(63) Continuation of application No. 11/477,969, filed on Jun. 28, 2006, now Pat. No. 8,388,573.

(51) Int. Cl.
*A61M 25/10* (2013.01)
*A61M 25/00* (2006.01)
(Continued)

(52) U.S. Cl.
CPC ......... *A61M 25/1002* (2013.01); *A61M 25/104* (2013.01); *A61M 25/0069* (2013.01); *A61M 2025/0081* (2013.01);
(Continued)

(58) Field of Classification Search
CPC ............ A61M 25/10; A61M 25/1002; A61M 25/104; A61M 2025/10; A61M 2025/1002; A61M 2025/105; A61M 2025/1051; A61M 2025/1075; A61M 2025/1081; A61M 2025/1086; A61M 25/0069; A61M 2025/1052; A61M 2025/0681; A61M 2025/0183; A61M 2025/0081
USPC ................................ 604/96.01, 97.01, 99.01, 604/103.01–103.03, 103.05–103.09, 509, 604/510; 623/1.11, 1.12, 1.42, 1.43
See application file for complete search history.

(56) References Cited

U.S. PATENT DOCUMENTS 5,250,070 A   10/1993   Parodi
5,498,238 A    3/1996   Shapland et al.
(Continued)

FOREIGN PATENT DOCUMENTS

EP        0511499 A2    3/1992
EP        0 567 788 A1  3/1993
(Continued)

OTHER PUBLICATIONS

Mitchel, Joseph F., et al., Enhanced Intracoronary Thrombolysis With Urokinase Using a Nove, Local Drug Delivery System, Circulation, 1995; 94: pp. 785-793.
(Continued)

*Primary Examiner* — Theodore Stigell
*Assistant Examiner* — Amber Stiles
(74) *Attorney, Agent, or Firm* — Randy Shen; Blakely, Sokoloff, Taylor & Zafman LLP (57) ABSTRACT

A catheter configured for delivering an agent to a patient's vessel wall is described. The catheter includes an inflatable balloon substantially covered by a expandable cage such that when the inflatable balloon is inflated the expandable cage substantially surrounds an outer surface of the inflated balloon. The inflatable balloon is configured to be deployed within a lumen against a lumen wall and separated from the lumen wall by the expandable cage in an expanded state, and is adapted to provide an agent delivery to a treatment site, and the expandable cage is further collapsible and is removable from said lumen.

9 Claims, 7 Drawing Sheets

(51) Int. Cl.
*A61M 25/01* (2006.01)
*A61M 25/06* (2006.01)

(52) U.S. Cl.
CPC ............... *A61M 2025/0183* (2013.01); *A61M 2025/0681* (2013.01); *A61M 2025/105* (2013.01); *A61M 2025/1052* (2013.01); *A61M 2025/1075* (2013.01)

(56) References Cited

U.S. PATENT DOCUMENTS

| | | | |
|---|---|---|---|
| 5,700,243 A * | 12/1997 | Narciso, Jr. | 604/102.01 |
| 5,863,284 A | 1/1999 | Klein | |
| 6,051,001 A * | 4/2000 | Borghi | A61F 2/958 |
| | | | 606/198 |
| 6,068,611 A | 5/2000 | Loffler et al. | |
| 6,540,721 B1 | 4/2003 | Voyles et al. | |
| 6,544,223 B1 | 4/2003 | Kokish | |
| 6,551,341 B2 | 4/2003 | Boylan et al. | |
| 6,623,452 B2 * | 9/2003 | Chien et al. | 604/103.01 |
| 6,645,135 B1 | 11/2003 | Bhat | |
| 6,695,813 B1 | 2/2004 | Boyle et al. | |
| 6,709,427 B1 | 3/2004 | Nash et al. | |
| 6,821,242 B1 | 11/2004 | Waksman et al. | |
| 6,899,729 B1 | 5/2005 | Cox et al. | |
| 6,913,612 B2 | 7/2005 | Palmer et al. | |
| 6,939,376 B2 | 9/2005 | Shulze et al. | |
| 2001/0014717 A1 | 8/2001 | Hossainy et al. | |
| 2002/0007209 A1 | 1/2002 | Scheerder et al. | |
| 2002/0007215 A1 | 1/2002 | Falotico et al. | |
| 2002/0051730 A1 | 5/2002 | Bodnar et al. | |
| 2002/0077592 A1 | 6/2002 | Barry | |
| 2002/0077594 A1 | 6/2002 | Chien et al. | |
| 2002/0082552 A1 * | 6/2002 | Ding et al. | 604/103.02 |
| 2002/0090388 A1 | 7/2002 | Humes et al. | |
| 2003/0153870 A1 * | 8/2003 | Meyer et al. | 604/96.01 |
| 2004/0049152 A1 * | 3/2004 | Nayak | 604/96.01 |
| 2004/0230176 A1 | 11/2004 | Shanahan et al. | |
| 2004/0249439 A1 * | 12/2004 | Richter et al. | 623/1.15 |
| 2005/0021071 A1 * | 1/2005 | Konstantino et al. | 606/194 |
| 2005/0038468 A1 | 2/2005 | Panetta et al. | |
| 2005/0106206 A1 * | 5/2005 | Herweck | A61L 29/16 |
| | | | 424/423 |
| 2005/0113907 A1 | 5/2005 | Fischell | |
| 2005/0175666 A1 | 8/2005 | Ding | |
| 2005/0256565 A1 | 11/2005 | Barry | |
| 2006/0030925 A1 * | 2/2006 | Pryor | 623/1.12 |
| 2008/0319415 A1 | 12/2008 | Shturman | |
| 2011/0054438 A1 | 3/2011 | Webster et al. | |

FOREIGN PATENT DOCUMENTS

| | | |
|---|---|---|
| EP | 0 712 615 A1 | 5/1996 |
| EP | 0 819 011 B1 | 3/2003 |
| WO | WO 97/16170 | 5/1997 |
| WO | WO 97/42998 | 11/1997 |
| WO | WO 02/26139 | 4/2002 |
| WO | WO 02/26281 | 4/2002 |
| WO | WO 02/49706 | 6/2002 |
| WO | WO 03/039612 | 5/2003 |

OTHER PUBLICATIONS

Moura, Alvaro, MD., et al., Intramural Delivery of Agent via a Novel Drug-Delivery Sleeve, Circulation, 1995; 95:pp. 2299-2305.
O, Tahlil, et al., The Dispatch catheter as a delivery tool for arterial gene transfer, Cardiovascular Research, Jan. 1977:33(1): pp. 181-187.

* cited by examiner

LOCAL DELIVERY WITH A BALLOON COVERED BY A CAGE

This application is a continuation of co-pending U.S. application Ser. No. 11/477,969, filed Jun. 28, 2006.

FIELD

The present invention relates generally to medical devices, and more particularly to an assembly for delivery of an agent to the coronary or peripheral vasculature.

BACKGROUND

In the treatment of diseased vasculature, therapeutic agents have commonly been administered, typically as part of other interventional therapies such as angioplasty or stent delivery. Local delivery, as opposed to systemic delivery, is a preferred method of treatment in that smaller total levels of medication are administered in comparison to systemic dosages, yet are concentrated at a specific site. As a result, local delivery produces fewer side effects and achieves more effective results.

A variety of methods and devices have been proposed for percutaneous drug delivery to a diseased region of the vasculature. For example, catheters having porous balloons can be used to deliver a therapeutic agent infused into the inflatable interior of the porous balloon and through the porous wall of the balloon. Alternatively, prostheses such as stents or other implantable devices provide for local drug delivery when coated or otherwise made to include a therapeutic agent which elutes from the implanted prosthesis. Another suggested method involves the use of one or more catheters having multiple balloons. The diseased region is isolated by inflating the balloons on either side of the diseased region, and the therapeutic agent is infused through a lumen of the catheter shaft and into the isolated diseased region from a delivery port on the catheter shaft located between the balloons.

One disadvantage with using a balloon to deliver drugs is that the balloons typically have a plain surface and therefore the contact to the artery wall is uniform and the whole endothelium receives the pressure of the balloon surface. Such contact causes endothelial damage/injury during the particular drug delivery procedure. Endothelial denudation (a loss of a surface layer) is associated with or representative of the endothelial damage caused by the balloon wall contact.

Another difficulty has been maximizing the amount of drug taken-up and retained at the diseased site, while minimizing the washout of large amounts of drug downstream of the treatment site. Drug washout reduces the efficiency of local intravascular drug delivery, in addition to causing potentially harmful systemic exposure to the drug. Therefore, it would be a significant advance to provide an improved device and method for providing therapy to a desired location within a patient's body lumen.

SUMMARY

Embodiments of the present invention are directed to an assembly deliverable by a catheter assembly configured for delivering an agent to a patient's vessel wall or lumen. The assembly includes an inflatable balloon housed by a soft expandable cage. A method is provided for treating the patient's vessel wall or lumen or vascular lumen by locally delivering the agent thereto.

In one embodiment, a catheter assembly configured for delivering an agent to a patient's vessel wall is provided. The catheter comprises an inflatable balloon substantially covered by a soft expandable cage such that when the inflatable balloon is inflated, the soft expandable cage resides on the outside of the inflated member. The inflatable balloon is configured to be deployed within a lumen against a lumen wall, and separated (or spaced) from the lumen wall by the soft expandable cage in an expanded state. The inflated balloon however, does not directly or substantially directly contact the lumen wall. The inflatable balloon isolates a treatment site within the lumen for an agent to be delivered thereto. In one embodiment, the inflatable balloon is itself adapted to deliver an agent to the treatment site (e.g., a microporous drug delivery balloon). In one embodiment, an additional device is advanced into the vessel at the treatment site and the agent is injected therethrough to the treatment site. The soft expandable cage is further collapsible and is removable from the lumen. As a result, the catheter provides for direct injection of the agent to the vessel wall (or other target tissue), minimizes drug washout in the vasculature, and prevents or eliminates endothelial damage/injury to the vessel.

The expandable cage is self-expandable, can be a stent-like structure, or can be similar to an embolic protection device, and is re-collapsible and removable from the vessel by a sheath. The expandable cage is comprised of struts configured to be radially expandable and collapsible. The struts are sufficiently thick to maintain or provide a separation between the vessel wall and the inflatable balloon once the balloon is inflated. The balloon and the cage, once deployed, form or isolate a space immediately adjacent thereto in the lumen wall for agent delivery.

The inflatable balloon can be similar to a microporous drug delivery balloon. The inflatable balloon can include ports for an agent to be eluted therefrom and to the vessel wall. The ports can be configured to deliver the agent in a desired direction. A separate injection device or a lumen provided in the catheter or independent from the catheter can also be used to inject an agent to the vessel wall in the space isolated by the inflated balloon and the cage. The inflatable balloon can be inflated by an injection of a fluid at a low pressure (e.g., less than about 2 atm). The inflatable balloon can also be attached at certain points to the inner area of the expandable cage so that when the cage is expanded, the movements of the struts pull or inflate the inflatable balloon. The inflatable balloon may be adapted to be intermittently inflated and/or deflated for suitable treatment applications (independent from the cage). The inflatable balloon can also be inflated slightly further after an agent or drug is delivered to the treatment site to further push, maintain, or press the agent toward and/or into the vessel wall. As a result of the inflatable balloon being deployed inside the cage and substantially separated or spaced from the vessel wall, the assembly minimizes or prevents endothelial injury and prevents complete denudation of the delivery area within the vessel.

The outer surface of the inflatable balloon (or other lining member) is separated or spaced from the vessel wall by the self-expanding cage therearound. Thus, injury to the vessel wall is minimized. The thickness of the self-expanding cage can be configured to control the amount of space or separation between the balloon and the vessel lumen wall.

The catheter assembly can be configured to allow for accessing the tortuous, narrow distal vasculature. In a presently preferred embodiment, a catheter of the invention is configured for delivery of an agent to a coronary artery or vein. However, the vasculature need not be coronary, can be, for example, renal, femoral, popliteal, carotid, cerebral or other arteries and veins, aneurysms and aneurismal sacs, and may include delivery to implanted devices therein such as grafts, stents and the like. Similarly, agent delivery may occur to the wall of a variety of tubular body lumens including pulmonary, gastrointestinal and urinary tract structures. Thus, the term "vessel" as used herein should be understood to refer generally to body lumens.

A variety of suitable agents can be delivered using the catheter(s) and method(s) of the invention, including therapeutic and diagnostic agents. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. As used herein, treatment agents are intended to include, but are not intended to be limited to, drugs, biologically active agents, chemically active agents, therapeutic agents, and the like, and pharmaceutical compositions thereof, which can be used to deliver a treatment agent to a treatment site as described herein. In particular, suitable therapeutic agents include, but are not limited to, thrombolytic drugs, anti-inflammatory drugs, anti-proliferative drugs, drugs restoring and/or preserving endothelial function, and the like. A variety of biologically active agents can be used including but not limited to peptides, proteins, oligonucleotides, cells, and the like. A variety of diagnostic agents can be used according to the present invention. According to the present invention, agents described herein may be provided in a variety of suitable formulations and carriers including liposomes, polymerosomes, nanoparticles, microparticles, lipid/polymer micelles, and complexes of agents with lipid and/or polymers, and the like. Suitable agent(s) may be pre-mixed or individually delivered to the site for mixing at the site, depending on desired treatments.

A catheter of the invention provides for improved delivery of drug therapy to the patient's vessel wall, by enhancing drug uptake into the vessel wall while minimizing drug washout into the vascular system. Further, the catheter is configured to minimize and/or eliminate endothelial injury to the vessel wall. These and other advantages of the invention will become more apparent from the following detailed description of the invention and accompanying exemplary drawings.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Exemplary embodiments of the present invention pertain to a catheter assembly that can be used to deliver an agent to a treatment site. In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

The assembly includes an inflatable balloon housed or substantially covered by a soft expandable cage. A method is provided for treating the patient's vessel wall or lumen or vascular lumen by locally delivering the agent thereto.

As mentioned, in one embodiment, a catheter configured for delivering an agent to a patient's vessel wall is provided. The catheter comprises an inflatable balloon substantially covered by a soft expandable cage such that when the inflatable balloon is inflated, the soft expandable cage resides on the outside of the inflated member. The inflatable balloon is configured to be deployed within a vessel lumen against a vessel lumen wall and separated (or spaced) from the vessel lumen wall by the soft expandable cage in an expanded state. The inflated balloon however, does not directly or substantially directly contact the vessel lumen wall. The inflatable balloon isolates a treatment site within the vessel lumen for an agent to be delivered thereto. In one embodiment, the inflatable balloon is itself adapted to deliver an agent to the treatment site (e.g., a microporous drug delivery balloon). In one embodiment, another catheter device is advanced into the vessel at the treatment site and the agent is injected therethrough to the treatment site. The soft expandable cage is further collapsible and is removable from the vasculature lumen. As a result, the catheter provides for direct injection of the agent to the vessel wall (or other target tissue), minimizes agent washout in the vasculature, and prevents or eliminates endothelial damage/injury to the vessel.

Figures 1A, 1B, 1C, 1D:
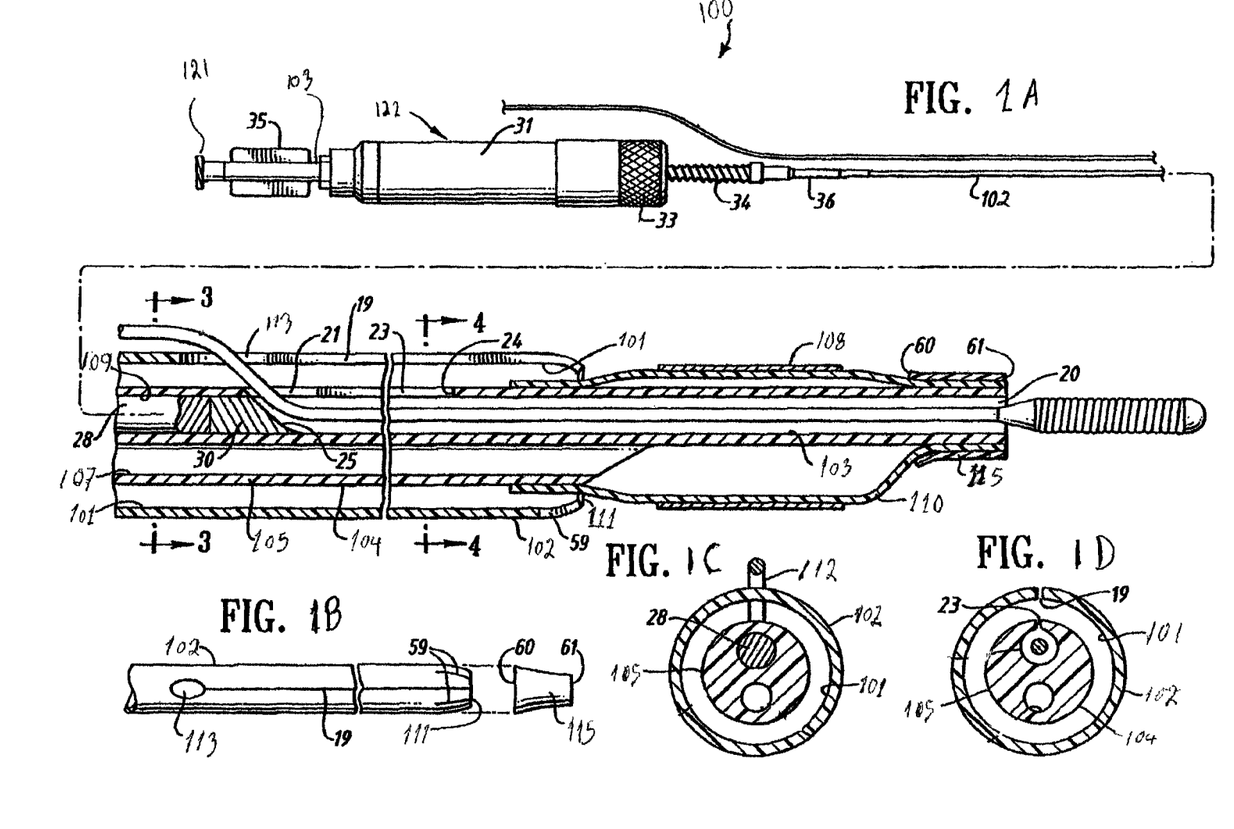
FIGS. 1A-1D illustrate an exemplary embodiment of a catheter delivery system comprising an inflatable balloon and a self-expanding cage surrounding the inflatable balloon.

A delivery system such as one illustrated in FIGS. 1A-1G can be incorporated and used to deliver the cage and the balloon to a vessel. It is to be appreciated that other systems can also be used and that existing improvements to the design described herein or other similar design could also be incorporated. In FIG. 1A, a catheter assembly 100 is provided which comprises a delivery sheath 102 and an intravascular catheter 104. The delivery system described herein is but an example of a delivery system that can be adapted to deliver the cage and balloon to a treatment site.

FIGS. 1A-1D illustrate a delivery system which embodies features of the invention. Generally, the delivery system includes the delivery sheath 102 which has an outer lumen 101 and the intravascular catheter 104 disposed within the outer lumen 101. The intravascular catheter 104 has an elongated catheter body 105 and a balloon 110 on the distal portion of the catheter body. A manipulating device or proximal handle 122 is provided on the proximal end of the delivery system which is employed to effect relative axial or longitudinal movement between the delivery sheath 102 and the intravascular catheter 104. A self-expandable cage 108, which is to be delivered within a patient's body lumen, is mounted on the exterior of the balloon 110. The cage 108 functions to space the balloon 110 away from the lumen to minimize immediate contact between the balloon 110 and the lumen wall while allowing sufficient proximity for an efficient delivery of an agent to the lumen. During the advancement of the delivery system through the patient's vascular system to the treatment area, the sheath 102 is tucked within an elastic cone 115. FIG. 1A shows the location of the elastic cone 115 after the relative axial positions of the sheath 102 and catheter 104 are adjusted to expose the expandable cage 108.

The delivery sheath 102 has a distal port 111 in its distal end which is in fluid communication with the outer lumen 101 and a proximal port 113 disposed proximally to the distal port. The distal portion of delivery sheath 102 tapers down in a spherical-like manner so that the cross-sectional area is somewhat less in the distal region than the cross-sectional area of the rest of the delivery sheath. A slit 19 extends from the proximal port 113 to a location just proximal to the distal port 111. In one embodiment, a plurality of slits 59 in the wall of sheath 102 extends a short distance from the distal port 111 as shown in FIG. 1B. As contemplated, the slits 59 would facilitate in the relative axial position adjustment of the sheath 102 and intravascular catheter 104.

The intravascular catheter 104 has a distal port 20 and a proximal port 21 which are in fluid communication with a first inner lumen 103 extending within the distal portion of the catheter 104 and being adapted to slidably receive a guidewire therein. A slit 23 extends from the proximal port 21 to a location 24 (FIG. 1G) proximal to the proximal end of balloon 110. The proximal end of the guidewire receiving first inner lumen 103 is provided with a ramp 25 to guide the proximal end of guidewire 112 out the proximal port 21 of intravascular catheter 104 when the catheter is mounted onto the guidewire, as will be discussed hereinafter. A second, much longer inner lumen 107 is provided within the catheter body 105 to direct an inflation fluid and/or an agent from the proximal end of the catheter body to the interior of the balloon 110.

Proximal to the proximal port 21 in the catheter body 105 is a stiffening member 28 which is disposed in third inner lumen 109 provided within the catheter body 105. As shown in the drawings, the third inner lumen and the first inner lumen 103 may be the same lumen with a plug 30 separating the two lumens. The ramp 25 is on the distal side of the plug 30.

Figure 1E:
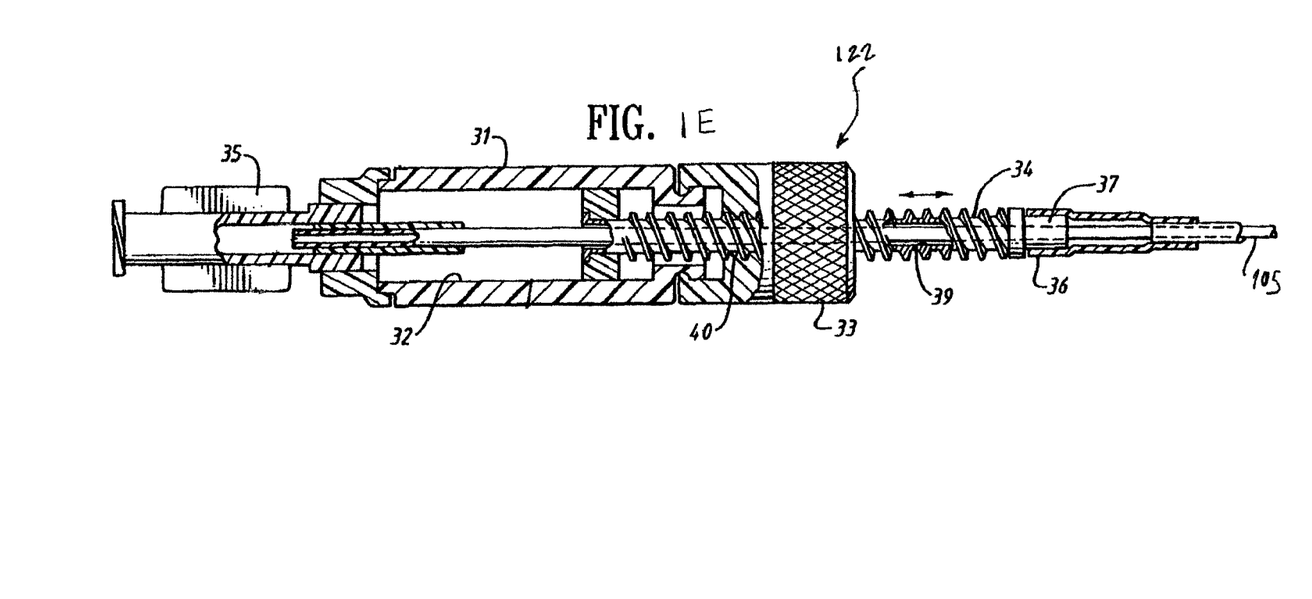
FIG. 1E illustrates an exemplary handle for the delivery system shown in FIG. 1A.

As illustrated in FIGS. 1A and 1E, the manipulator 122 on the proximal end of the delivery system has a housing 31 with an interior chamber 32, a cap 33 rotatably mounted onto the distal end of the housing 31, an elongated drive member 34 which has male threads on the exterior thereof and which is at least partially disposed within the interior chamber 32 and a Luer lock 35 which is fixed within the proximal end of the housing 31. The proximal end 36 of the sheath 102 is secured to the distal end 37 of the elongated drive member 34 which extends out of the distal end of the housing 31. As shown in more detail in FIG. 1E, the proximal end 106 of the catheter body 105 passes through passageway 39 in the elongated drive member 34 and is fixed within the Luer lock 35 by suitable means such as adhesive. The cap 33 which is rotatably mounted onto the distal end of the housing 31 is provided with an inner threaded collar 40 adapted to threadably engage the threaded exterior of the elongated driving member 34. Rotation of the cap 33 moves the driving member 34 axially to thereby effect relative axial movement between the sheath 102 and the intravascular catheter 104.

Figure 1F:
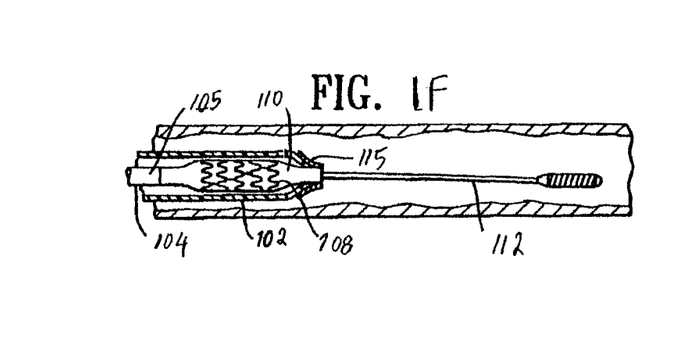
FIGS. 1F-1G illustrate an exemplary application of delivering the system shown in FIGS. 1A-1D to a vessel lumen.

In a typical situation, the delivery system of the invention is used to deliver an agent to the blood vessel. In these situations there will usually be a guidewire 112 (or other guiding member) in place extending across the treatment site of the artery such as shown in FIG. 1F. The proximal end of the guidewire 112, which extends out of the patient during the entire procedure, is inserted through the elastic cone 115 by threading the guidewire 112 into the small aperture 61 and out the large aperture 60 of the cone 115 as shown in FIG. 1B. The guidewire 112 is then inserted through the distal port 20 in the distal end of the intravascular catheter 104 and advanced proximally through the first inner lumen 103 until the proximal end of the guidewire 112 impacts the ramp 25 and is thereby directed through the proximal port 21.

The intravascular catheter 104 is preferably positioned within the outer lumen 101 of the delivery sheath 102 so that at least a significant portion of the proximal port 113 in the sheath is in alignment with the proximal port 21 of the intravascular catheter. In this manner, proximal advancement of the guidewire 112 through the inner lumen 103 will also direct the proximal end of the guidewire 112 out the proximal port 113 in the delivery sheath 102. The sheath 102 is then tucked within the elastic cone 115 by inserting the distal end of sheath 102 into the proximal end and large aperture 60 of the cone 115. The proximal end of the guidewire 112 may then be manually held to maintain the position of the guidewire 112 within the patient's vasculature, while the delivery system is advanced over the guidewire 112 and through the patient's vascular system. The function of the elastic cone 115 is to facilitate the advancement of the delivery system. By tucking the distal end of sheath 102 within the cone 115 as shown in FIG. 1F, the delivery system has a profile suited for successfully maneuvering about the sharp turns and angles of the patient's vasculature. The advancement of the delivery system continues until the distal ends of the catheter and sheath extend adjacent to or across the treatment site. Next, the manipulator 122 on the proximal end of the delivery system is actuated by rotating the cap 33 on the proximal end of the housing 31 to move the sheath 102 proximally with respect to the catheter 104 and thereby expose and deploy the cage 108 that covers the balloon 110. The elastic cone 115 thereby disengages the sheath 102 and collapses in engagement about the distal portion of the catheter 104 as is shown in FIG. 1.

Figure 1G:
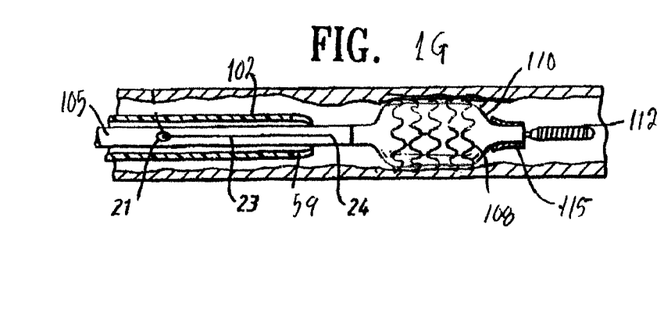

When the balloon 110 and the cage 108 surrounding the balloon are properly placed at the treatment site, the cage 108 is expanded or allowed to be self-expanded. The balloon 110 can be expanded by an inflation fluid (by a low pressure, e.g., <2 atm) through the handle 122 or the Luer lock 35. In one embodiment, the cage 108 is self-expanded and can be configured to pull the balloon 110 open when the cage is expanded. Alternatively, a low pressure is used to expand the balloon 110. FIG. 1G shows the cage 108 expanded to engage the lumen wall and the balloon 110 expanded within the cage 108 and not in immediate or substantial contact with the lumen wall. An agent can then be delivered to the lumen wall (e.g., via elution from the balloon or separate injection).

Figure 2:
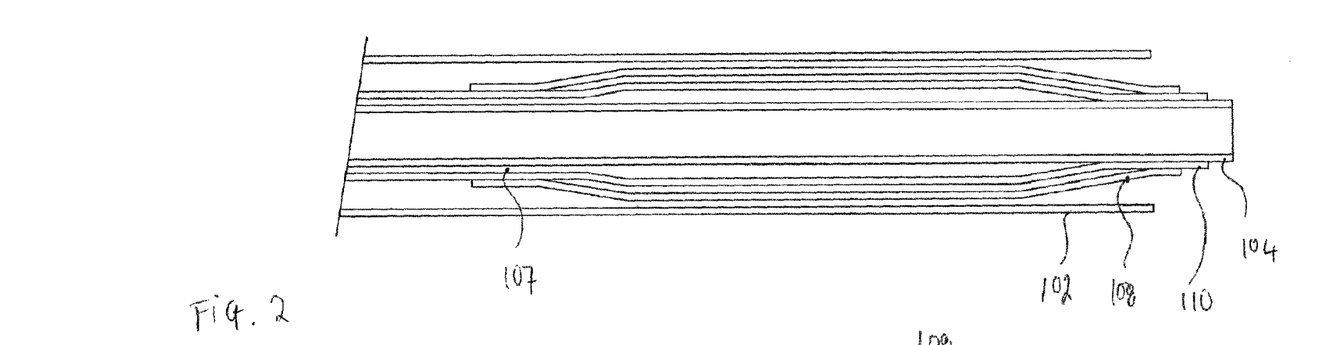
FIG. 2 illustrates the self-expanding cage surrounding the balloon in an unexpanded form.
Figure 3:
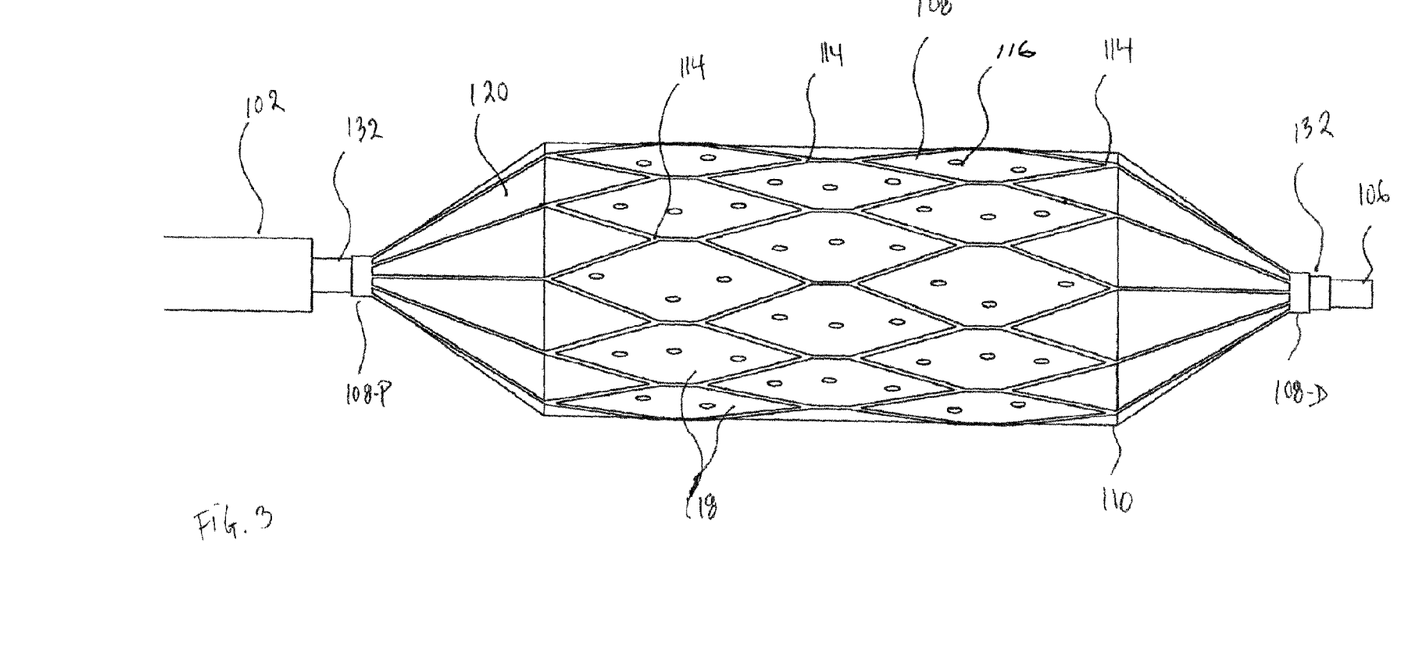
FIG. 3 illustrates the self-expanding cage surrounding the balloon in an expanded form.

FIGS. 2-3 illustrate, respectively, a section of the assembly 100 showing the inflatable balloon 110 and the cage 108 in their compressed/unexpanded and expanded state. In one embodiment, the cage 108 is fixed at one end (108-D) to a neck member 132, which is slidably disposed over the intravascular catheter 104. The cage 108 can also be fixed at the proximal end (108-P) to the neck member 132 as shown in FIG. 3. The cage 108 may be configured so as to be slideable along the intravascular catheter 104. In its collapsed state, the cage 108 collapses onto the outer surface of the intravascular catheter 104 and in its expanded state, the cage 108 radially and/or longitudinally expands therefrom.

As mentioned, a guidewire 112 is provided, within the intravascular catheter 104 to facilitate maneuvering the assembly 100 within a patient's body lumen. As illustrated herein or previously, the guidewire system is a rapid-exchange type of guiding system. It is to be appreciated, however, that other types such as over the wire type system known in the art can also be used. In one embodiment, the guidewire 112 is maneuvered to the treatment site first and the catheter assembly 100 is tracked over the guidewire member 112 previously placed at the treatment site. The intravascular catheter 104 may be configured with a guidewire lumen as previously described therein for slidably advancing over the guidewire 112. The guidewire 112 and the delivery sheath 102 extend outside of the patient during a typical procedure.

The catheter delivery system 100 is delivered to a vessel in a low profile system as shown in FIGS. 1A, 1F, and 2. In these figures, the soft expandable cage 108 is in its collapsed, unexpanded, or compressed state. The inflatable balloon 110 is also in its collapsed or unexpanded state. The delivery sheath 102 constrains the cage 108 in its compressed or unexpanded form for the delivery.

In FIG. 3, at the treatment site, the soft expandable cage 108 is expanded as the delivery sheath 102 is proximally retracted. The inflatable balloon 110 is also inflated after the cage 108 is expanded and deployed.

The cage 108 is deployed by the manipulation of the proximal handle or manipulator 122. For example, the housing 31 of the manipulator 122 can be held in the palm of the physician's hand, with the thumb and index fingers thereof used to rotate cap 33 and thereby cause the necessary relative motion between the sheath 102 and intravascular catheter 104 to expose the cage 108. Retracting the sheath 102 relative to the intravascular catheter 104 allows the cage 108 to self-expand. An inflation device, such as described in U.S. Pat. No. 4,439,185, can be used to inject inflation fluid through Luer lock 35 into the interior of the balloon 110. It is to be appreciated that other known manipulators can also be used to deploy the cage and the balloon. Upon completion of the treatment, the manipulator 122 can again be actuated by the physician rotating cap 33 with the fingers of the hand holding the manipulator 122, to cause relative rotation between the intravascular catheter 104 and the sheath 102, to pull the intravascular catheter 104 back into the distal end of the sheath 102 (or pushing the distal end of the sheath over the distal end of the intravascular catheter 104, depending upon the perspective). The entire assembly, including the cage 108, balloon 110, and the guidewire 112, can then be removed from the patient.

The soft expandable cage 108 is a structure that is expandable with minimal force and does not expand with a great pressure that may cause damage to the lumen that it is deployed within. A conventional stent-like structure and an embolic device are known to be self-expandable with minimal force impacting the lumen wall. Further, the strut assembly of the cage can be configured to expand with minimal force toward the lumen wall. As used in the embodiments of the present invention, the cage 108 is not only expandable to be deployed against the lumen wall for the duration of the treatment and use of the catheter assembly 100, but is also re-compressible or re-collapsible to allow it to be removed form the lumen. Such features distinguish the cage 108 from a conventional stent-like structure. The cage 108 is thus configured so that it can be retracted into the delivery sheath 102. Embodiments of the present invention describe a soft expandable cage 108 that is expanded to minimize the contact area or to prevent the surface of a balloon to rest on the wall of the vessel. The cage 108 thus separates and/or spaces the balloon from the lumen wall. In one embodiment, the cage 108 thus includes struts that are sufficiently thick to provide a clearance space between the balloon surface and the lumen wall. In one example, the struts of the cage 108 can have a thickness ranging from 0.002-0.012 inches, optimally, 0.004-0.006 inches. Even though the struts of the cage 108 is thick, the strut assembly is made to be soft so that deploying the cage 108 would not cause an undesired impact on the inner wall of the lumen. The balloon 110 is still expanded enough to reduce blood flow distally to the balloon (thus minimizes agent wash-out) and to bring the balloon 110 sufficiently close to the lumen wall for delivery of an agent.

The soft expandable cage 108 comprises an assembly of struts 114 made of a shape memory material such as nickel-titanium alloy (NiTi). The struts' configuration provided the cage 108 with a first shape that is collapsed or compressed (FIGS. 1A and 2) for delivery, and a second shape that is radially expanded and uncompressed (FIG. 3) utilizing the sheath or a delivery sheath 102. The delivery sheath 102 enables the cage 108 to be transported to the treatment site in a compressed or unexpanded state wherein retraction of the sheath 102 over the cage 108 allows it to radially expand and advancing the sheath 102 over the cage 108, compresses it, and
allows it to be removed.

The pattern of the strut assembly is configured to provide the cage 108 with an ability to collapse and expand easily similar to a stent or an embolic protection device. The configuration of the struts is also such that the delivery sheath 102 can easily slide over the cage 108 to collapse the cage 108 and slide off the cage 108 to allow it to expand.

The soft expandable cage 108 can be made using similar methods used to make an embolic protection device as is known in the art. The cage 108 is made of the expandable strut assembly made of NiTi and includes a number of outwardly biased and extending struts 114 that are capable of self-expansion from compressed or collapsed position as previously described to an expanded or deployed position within a patient's vasculature or vessel.

In one embodiment, the cage 108 includes the proximal end 108-P which is optionally rotatably attached to the outer surface of the neck member 132. The distal end 108-D translates along the neck member 132 whenever the struts 114 move between the expanded and contracted position.

The cage 108 can be formed to include a tubular body and the assembly of struts 114 such that the struts project radially outward in an unstressed or uncompressed state. Laser cutting and/or other suitable techniques can be used to form the cage 108.

In one embodiment, the inflatable balloon 110 is attached to the inner area of the cage 108. FIGS. 2-3 show the cage 108 expanded and the inflatable balloon 110 being expanded within the inner area of the cage 108. The inflatable balloon 110 may be attached to the cage 108 at several points using conventional attachment means (e.g., adhesive). The inflatable balloon 108 can be inflated from a collapsed or unexpanded configuration (e.g., by a fluid injection or by the act of the expanded cage 108). The inflatable balloon 110 can be independently inflated after the soft expandable cage 108 is expanded. Once inflated, the inflatable balloon 110 resides within the radial perimeter of the expanded cage 108. The inflatable balloon 110 can be inflated using a low pressure, such as supplied by a fluid injection (the pressure should be less than 2 atm). Alternatively, the inflatable balloon 110 can be inflated from the collapsed configuration via the movement of the expandable struts 114 similar to that of an umbrella, except that the inflatable balloon 110 is an enclosed structure.

In one embodiment, the inflatable balloon 110 is porous having micro-pores or openings 116 for agents (e.g., a therapeutic drug) to elute from the inflatable balloon 110 toward the lumen wall or the treatment site (FIG. 3). The inflatable balloon 110 can be a conventional microporous balloon currently used in balloon drug-delivering device. The inflatable balloon 110 is compliant and can inflate with a relatively low pressure, e.g., 2 atm. In one embodiment, the inflatable balloon 110 includes cavities 120 so that a fluid can be communicated therethrough for inflation. The inflatable balloon 110 can be configured to inflate and deflate intermittently. The inflatable balloon 110 can be inflated independently from the cage 108 so that the pressure exerted onto the lumen wall by the inflation of the inflatable balloon 110 can be controlled so as to not cause an impact on the lumen wall. For example, the cage 108 can be deployed to engage the lumen wall and then the inflatable balloon 110 is inflated to deliver the agent proximate to the lumen wall. The inflatable balloon 110 needs not be inflated to physically contact the lumen wall.

Figure 4:
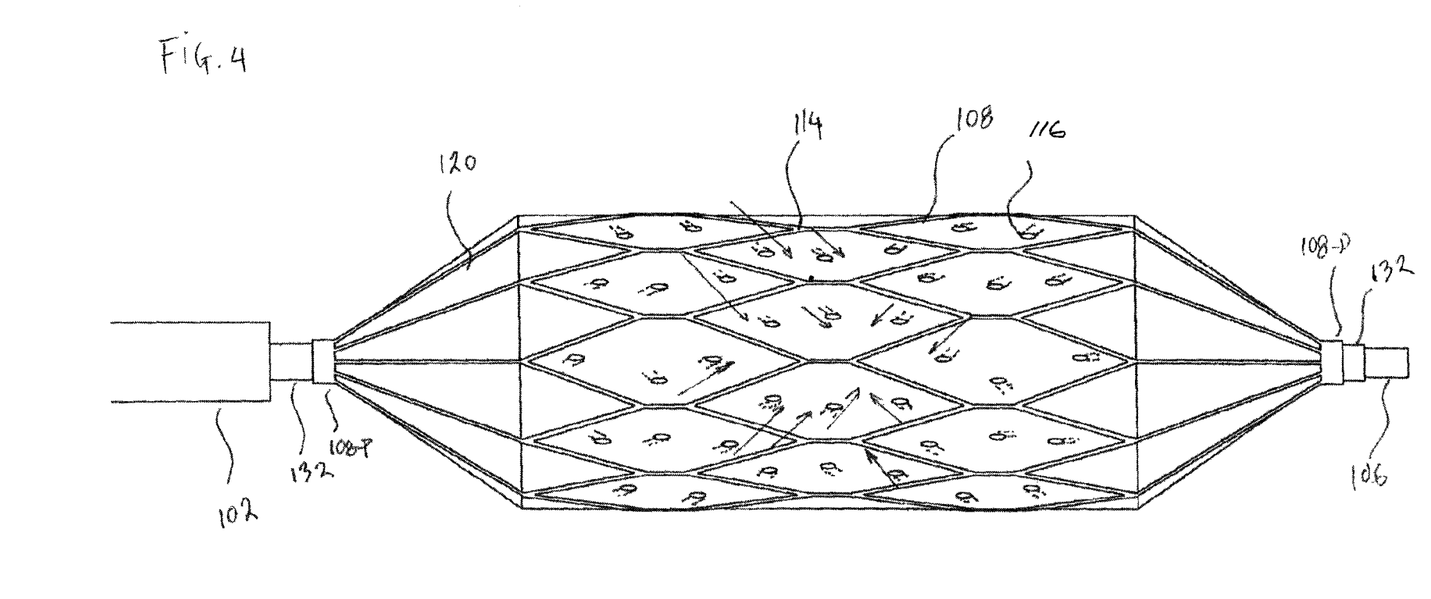
FIG. 4 illustrates the self-expanding cage surrounding the balloon in an expanded form with the balloon having pores with angled directions.

In one embodiment, an agent or agents to be delivered to the treatment site are placed in a chamber or compartment 118 provided in the inflatable balloon 110. In one embodiment, the openings 116 are configured to have a directional eluting path as illustrated in FIG. 4. In this figure, eluting paths leading to the openings 116 are "angled" so that agent eluting from the balloon through the openings 116 would tend to flow in the direction of the angles. This way, the agent to be delivered can be directed towards a certain site as desired by a certain treatment. This is also useful when two or more agents are to be delivered and mixed at the site. Such directional eluting paths increase mixing efficiency (a more detailed view can be seen at FIG. 4).

A variety of suitable agents can include therapeutic and diagnostic agents. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of biologically active agents can be used including but not limited to peptides, proteins, oligonucleotides, cells, and the like. A variety of other diagnostic agents not mentioned herein can of course be used according to the present invention. According to the present invention, agents described herein may be provided in a variety of suitable formulations and carriers including liposomes, polymerosomes, nanoparticles, microparticles, lipid/polymer micelles, and complexes of agents with lipid and/or polymers, and the like.

The delivery sheath 102 should have sufficient elasticity to resist the outward bias of the struts 114. The proper size and wall thickness of the delivery sheath 102 can be selected to provide such sufficient elasticity. The material of the delivery sheath 102 can also be chosen from the type of elastic material that has sufficient resilience to resist the expansive forces of the struts 114 held therein. Suitable materials used for the delivery sheath 102 are available and known in the art.

Referring to FIG. 1A, one or more injection port 103 can be provided and connected to the proximal handle 122. A conventional syringe 121 may be connected to the injection port 103 so as to communicate a fluid into the port. The injection port 103 can be used to communicate fluid, liquid, gas, or air into a lumen provided in the inflatable balloon 110 to inflate the balloon 110. The injection port 103 can also be used to communicate an agent or drug into another one or more lumen provided in the inflatable balloon 110 or in the catheter body 102 to deliver the agent to the treatment site in the vessel lumen.

When expanded, the balloon 110 is surrounded by the uncompressed or expanded cage 108 (FIG. 3-4). The inflatable balloon 110 may be inflated and still needs not be attached to the inner space of the cage 108. Alternatively, the inflatable balloon 110 is attached to the interior of the cage 108 such that when the cage 108 is uncompressed, the balloon 110 is pulled open.

FIGS. 5-8 show various possible configurations of the inflatable balloon 110 and the expandable cage 108 as they are deployed within a vessel lumen 142. In each case, the cage and the inflatable balloon are deployed within the vessel lumen 142 at the treatment site.

Figure 5:
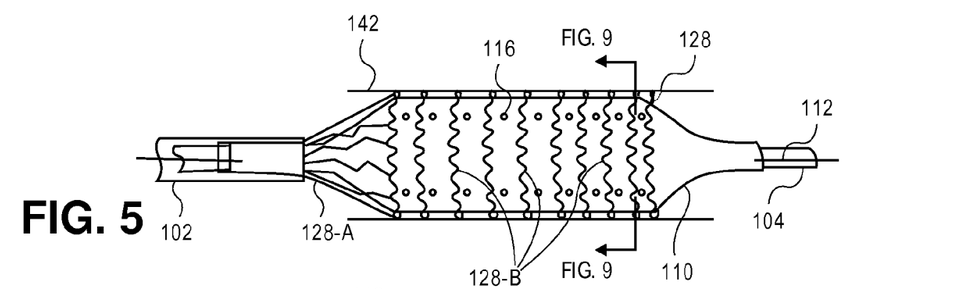
FIG. 5 illustrates an exemplary embodiment of a catheter assembly comprising an inflatable balloon and a self-expanding cage surrounding the inflatable balloon wherein the cage has a stent-like configuration.

FIG. 5 shows a cage 128 with a tapered (or non-tapered) tubular distal section and a proximal section. The cage 128 does not form a closed end at the distal section and may resemble a conventional stent structure with a cylindrical configuration at the distal section. The cage 128 includes an assembly of struts 128-B that forms the tubular and non-tapered distal section and the elongated struts 128-A that form the proximal section. The tubular distal section has a configuration similar to that of a conventional stent. The proximal section of the cage 128 allows the cage 128 to be collapsible back into the delivery sheath 102 for removal from the lumen 142. As shown in this figure, the cage 128 is expanded and surrounds an inflatable balloon 110. Both the cage 128 and the inflatable balloon 110 are supported by and attached to the inner member 104 of the catheter assembly 100 as previously described. As can be seen, the cage 128 prevents the inflatable balloon 110 from resting or contacting directly and fully against the inner wall of the vessel lumen. This way, a drug eluting from the inflatable balloon 110 or otherwise injected would be efficiently delivered to the treatment surface without the balloon surface resting on the lumen wall directly. After the cage 128 and the inflatable balloon 110 are fully deployed and the drug delivered to the treatment area, the inflatable balloon 110 can be slightly inflated further to press the agents against the vessel lumen wall if necessary. Once the inflatable balloon 110 is inflated, blood flow is reduced or blocked from flowing across the treatment area (or flowing down stream) from the proximal end of the vessel. This way, the agents or drugs can be concentrated or retained at the treatment site for the duration of the treatment. The inflatable balloon 110 and the cage 128 thus function to isolate the treatment area in the vessel, deliver an agent to the treatment site, and minimize drug-wash while preventing or eliminating endothelial damage typically caused by the inflation or contact of a conventional deployment of a balloon. In one embodiment, the inner member 104 is configured to include one or more perfusion openings to allow for some blood flow across an inflated member 110. In another embodiment, the balloon 110 is intermittently, as the particular treatment or diagnostic circumstances dictate or require, deflated and inflated to allow blood flow and to provide intermittent treatment when necessary.

Figure 6:
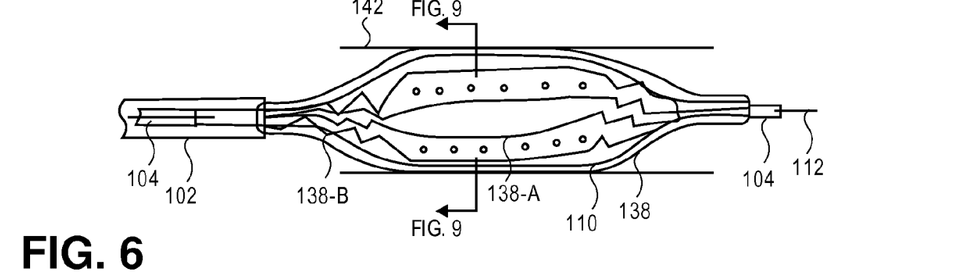
FIG. 6 illustrates an exemplary embodiment of a catheter assembly comprising an inflatable balloon and a self-expanding cage surrounding the inflatable balloon wherein the cage has a configuration similar to an embolic device.
Figure 9:
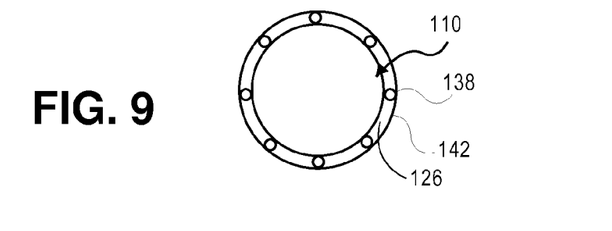
FIG. 9 illustrates a cross-sectional view of the inflatable balloon and the self-expanding cage deployed in a vessel.

FIG. 6 shows a cage 138 with an oblong-like distal section and a proximal section. The cage 138 has both the distal end proximal section forming tapered ends similar to an embolic protection device (or similar to the construction shown in FIGS. 3-4). The cage 138 includes an assembly of struts 138-B that forms the distal section and proximal section. The mid section of the cage 138 includes an assembly of struts 138-A that forms elongated strut lines. The mid section of the cage 138 may be designed to prevent any direct contact between the inflatable balloon and the lumen wall while the distal and proximal section allow for the collapsing and expansion of the cage 138. For example, as shown in FIG. 9, an illustration of the cross-sectional view of the inflatable balloon and the cage being deployed in the vessel, the inflatable balloon 110 is not in a direct contact with the vessel wall 142. A space 126 is provided between the outer surface of the inflatable balloon 110 and the lumen wall 142. As described above, the cage 138 is expanded and surrounds the inflatable balloon 110. Both the cage 138 and the inflatable balloon 110 are supported by and attached to the inner member 104 of the catheter assembly 100 as previously described. As can be seen, the cage 138 prevents the inflatable balloon 110 from resting or contacting directly and fully against the inner wall of the vessel lumen. This way, a drug eluting from the inflatable balloon 110 or otherwise injected would be delivered to the treatment surface and to the space 126. After the cage 138 and the inflatable balloon 110 are fully deployed and the drug delivered to the treatment area, the inflatable balloon 110 can be slightly inflated further to press the agents against the vessel lumen wall if necessary. Once the inflatable balloon 110 is inflated, blood flow is reduced or blocked from flowing across the treatment area from the proximal end of the vessel. This way, the agents can be concentrated or retained at the treatment site for the duration of the treatment. The inflatable balloon 110 and the cage 138 thus function to isolate the treatment area in the vessel, deliver an agent to the treatment site, and minimize drug wash-out while preventing or eliminating endothelial damage typically caused by the inflation or contact of a conventional deployment of a balloon. In one embodiment, the inner member 104 is configured to include one or more perfusion openings to allow for some blood flow across an inflated member 110. In one embodiment, the balloon 110 is intermittently, as the particular treatment or diagnostic circumstances dictate or require, deflated and inflated to allow for blood flow and to provide intermittent treatment when necessary.

Figure 7:
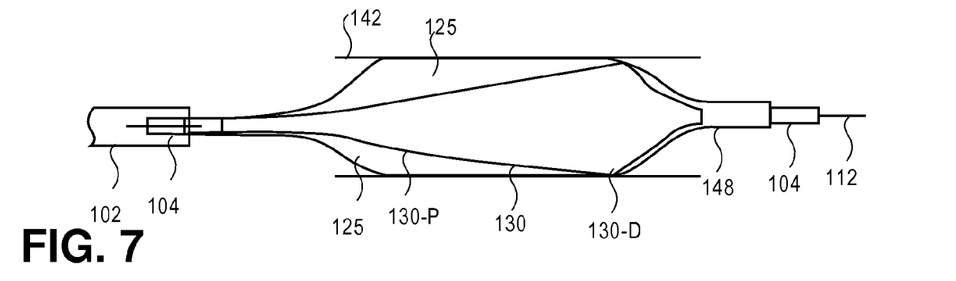
FIG. 7 illustrates an exemplary embodiment of a catheter assembly comprising an inflatable balloon and a self-expanding cage surrounding the inflatable balloon wherein the inflatable balloon is tapered with a larger distal end and smaller proximal end.

FIG. 7 shows a cage 148, which can have any one of the cage configurations previously described. In the present embodiment, a tapered inflatable balloon 130 is provided. The inflatable balloon 130 is similar to previously described with the addition of a tapered body configuration. The inflatable balloon 130 includes a distal section 130-D and a proximal section 130-P. The distal section 130-D has a larger outer diameter compared to the proximal section 130-P of the inflatable balloon 130. The balloon body between the distal and proximal sections is thus tapered from large to small (distal to proximal as illustrated in FIG. 7). When inflated following the deployment of the cage 148, the distal section is slightly larger so that it can seal off the blood flow in the distal direction or down stream from the distal section 130-D. A space 125 is provided between the outer surface of the inflatable balloon 130 and the lumen wall 142 at the proximal section 130-P. An agent can be injected or eluted into the space 125. The inflatable balloon 130 can also be porous with the capability of delivering the agent similar to previously described. Alternatively, the inflatable balloon 130 can simply be a balloon used to seal off blood flow and the agent is independently delivered or injected into the space 125 using a suitable technique. As described above, the cage 138 is expanded and surrounds the inflatable balloon 130. The inflatable balloon 130 is configured so that the space 125 is even larger for greater drug delivery capacity. Additionally, the inflatable balloon 130 is also configured to be able to seal off blood flow during treatment. Both the cage 148 and the inflatable balloon 130 are also supported by and attached to the inner member 104 of the catheter assembly 100 as previously described. As can be seen, the cage 148 prevents the inflatable balloon 130 from substantially resting or contacting directly and fully against the inner wall of the vessel lumen. In the present embodiment, the inflated balloon 130 is only touching the vessel lumen wall at the section 130-D, which functions to seal off the blood flow. This way, a drug eluting from the inflatable balloon 130 or otherwise injected would be delivered to the treatment surface and to the space 125. After the cage 148 and the inflatable balloon 130 are fully deployed and the drug delivered to the treatment area, the inflatable balloon 130 can be slightly inflated further to press the agents against the vessel lumen wall if necessary. Once the inflatable balloon 130 is inflated, blood flow is reduced or blocked from flowing across the treatment area from the proximal end (or down stream) of the vessel. This way, the agents or drugs can be concentrated or retained at the treatment site for the duration of the treatment. The inflatable balloon 130 and the cage 148, thus function to isolate the treatment area in the vessel, deliver an agent to the treatment site, and minimize drug-wash while preventing or eliminating endothelial damage typically caused by the inflation or contact of a conventional deployment of a balloon. In one embodiment, the inner member 104 is configured to include one or more perfusion openings to allow for some blood flow across an inflated member 130. In another embodiment, the balloon 130 is intermittently, as the particular treatment or diagnostic circumstances dictate or require, deflated to allow for blood flow and to provide intermittent treatment when necessary.

Figure 8:
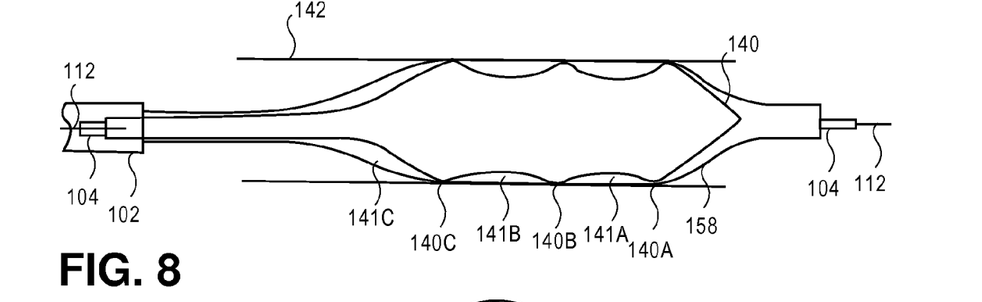
FIG. 8 illustrates an exemplary embodiment of a catheter assembly comprising an inflatable balloon and a self-expanding cage surrounding the inflatable balloon wherein the inflatable balloon comprise multiple sections.

FIG. 8 shows a cage 158, which can have any one of the configurations previously described. In the present embodiment, an inflatable balloon 140 is provided. The inflatable balloon 140 comprises of multiple sections 140A-140C. The inflatable balloon 140 is particularly useful for compartmentalizing the drug delivery area. The inflatable balloon 140 can be configured so that multiple different or same drugs/agents can be delivered independently to different points in the vessel lumen 142. In one embodiment, the sections 140A-104C are dimensioned so as to create spaces 141A, 141B, and 141C where the inflatable balloon 140 outer surface does not contact the inner wall of the lumen 142 and whereas the sections 140A-C are able to seal off blood flow once the inflatable balloon 140 is inflated. In the present embodiment, the assembly can be delivered so that one can compartmentalize the drug/agent delivery via the inflatable balloon 140. Generally, the sections 140A-C has larger outer diameters compared to the sections 141A-C. When inflated following the deployment of the cage 158, the section 140A-C are slightly larger or larger so that they each can substantially seal off the blood flow in their distal direction or downstream therefrom. An agent or drug can be injected into the spaces 141A-C. The inflatable balloon 140 can also be porous with the capability of delivering the agent similar to previously described. Alternatively, the inflatable balloon 140 can simply be a balloon used to seal off blood flow at certain sections and the agent is independently delivered or injected into the spaces 141A-C using a suitable technique. The catheter assembly 100 can also be made to include perfusion paths to allow blood flow to a certain sections if desired. As described above, the cage 158 is expanded and surrounds the inflatable balloon 140. Both the cage 158 and the inflatable balloon 140 are also supported by and attached to the inner member 104 of the catheter assembly 100 as previously described. As can be seen, the cage 158 prevents the inflatable balloon 140 from substantially resting or contacting directly and fully against the inner wall of the vessel lumen 142. This way, a drug/agent eluting from the inflatable balloon 140 or otherwise injected would be delivered to the treatment surface and to the designated spaces. After the cage 158 and the inflatable balloon 140 are fully deployed and the drug or drugs delivered to the treatment area, the inflatable balloon 140 can also be slightly inflated further to press the agents against the vessel lumen wall if necessary. Once the inflatable balloon 140 is inflated, blood flow is reduced or blocked from flowing across the treatment area from the proximal end of the vessel. This way, the agents or drugs can be concentrated or retained at the treatment site for the duration of the treatment. The inflatable balloon 140 and the cage 158 thus function to isolate and compartmentalize the treatment areas in the vessel, deliver an agent or agents to the treatment site, and minimize drug-wash while preventing or eliminating endothelial damage typically caused by the inflation or contact of a conventional deployment of a balloon. In one embodiment, the inner member 104 is configured to include one or more perfusion openings to allow for some blood flow across the inflated member 140. In one embodiment, the balloon is intermittently, as the particular treatment or diagnostic circumstances dictate or require, deflated and inflated to allow for blood flow and to provide intermittently treatment when necessary.

The shaft tubular members (e.g., the catheter body) for any of the embodiments herein can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Lumens can be formed in the tubular members using techniques known in the art. The tubular members may have walls made to comprise supporting braids or structures that provide flexibility while preventing crushing or kinking as the catheter is maneuvered to the site.

Figure 10A:
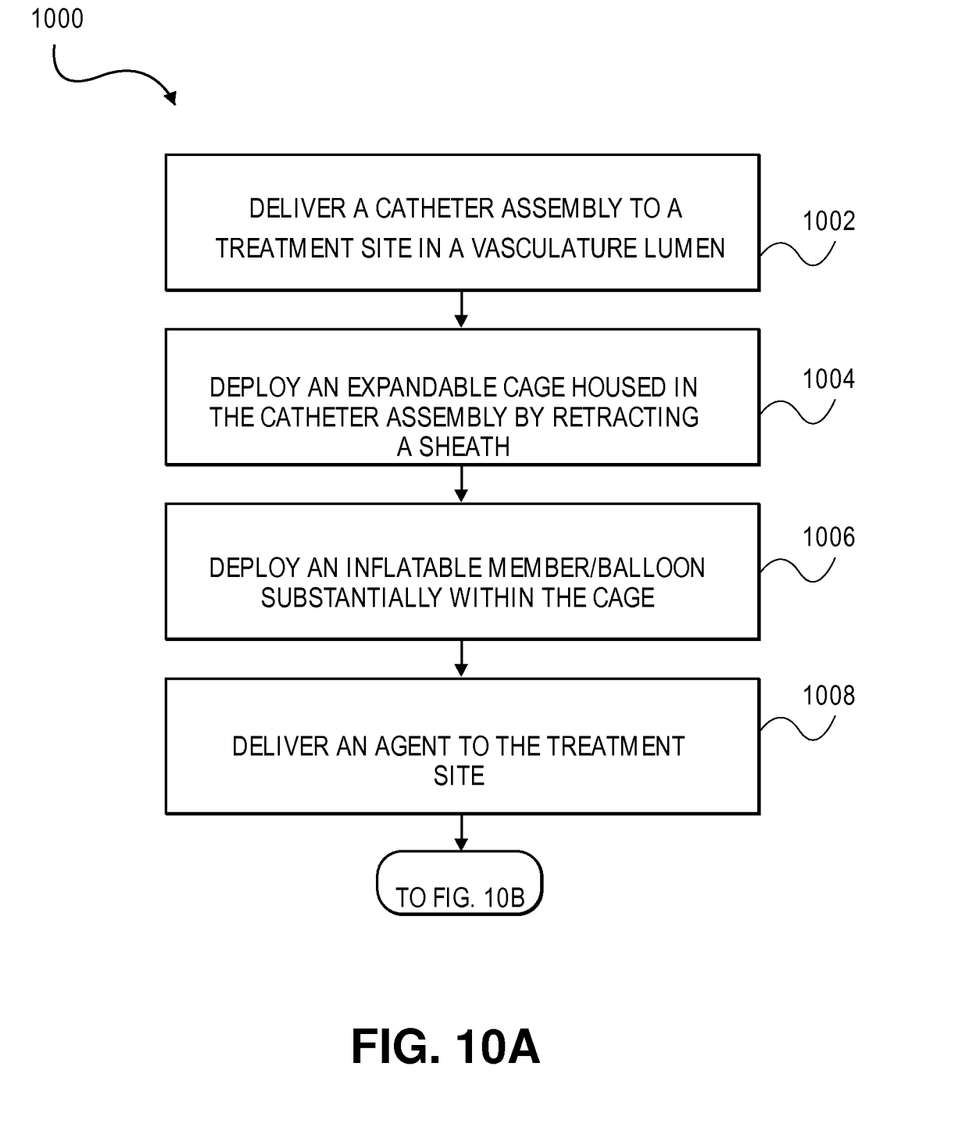
FIGS. 10A-10B illustrate an exemplary method of delivering an agent to a treatment site in according to embodiments of the present invention.
Figure 10B:
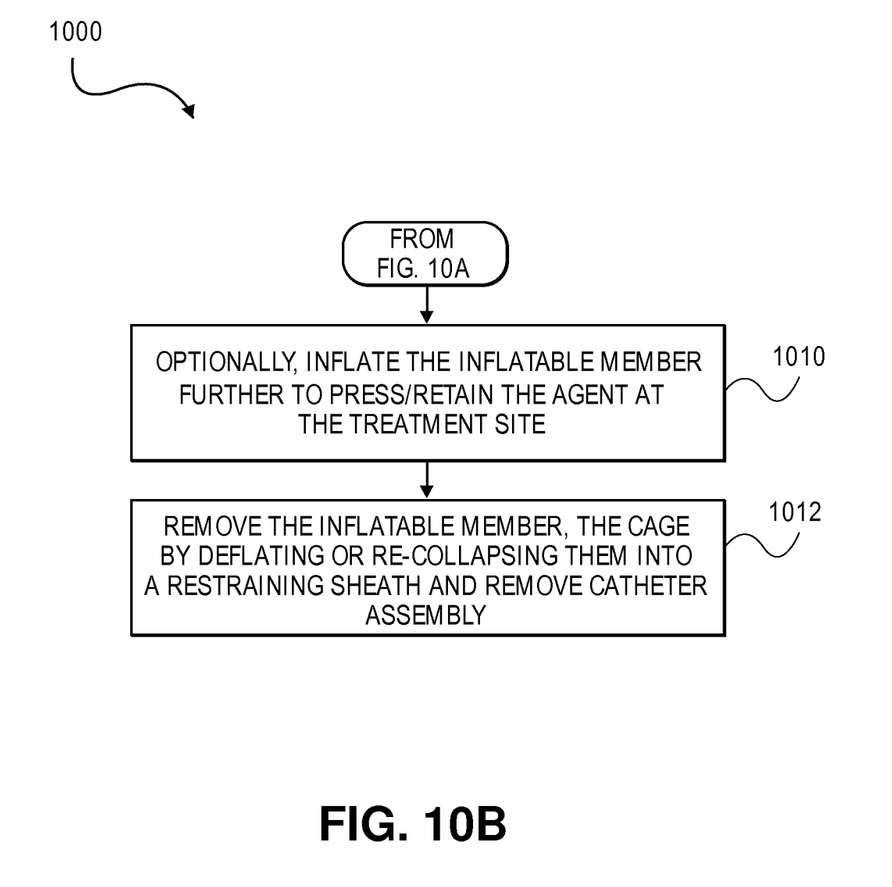

FIGS. 10A-10B illustrate an exemplary method 1000 of delivering an agent to a vessel lumen in accordance to embodiments of the present invention. At 1002, a catheter assembly (such as the catheter assembly 100 described above) is delivered to the treatment site in the vasculature lumen. In one embodiment, the catheter assembly is moved to the treatment site over a guidewire, which may already be placed across the treatment site. Generally, the catheter assembly comprises an inflatable balloon substantially covered by a soft expandable cage such that when the inflatable balloon is inflated the soft expandable cage resides on the outside of the inflated member as previously described. Preferably, the cage is expanded prior to the balloon being inflated.

At 1004, the expandable cage is deployed against the lumen wall. The expandable cage is self-expandable and can be deployed by the removal of a restraining or delivery sheath used to maintain the cage in a compressed state for delivery to the treatment site as previously described. At 1006, after the expandable cage is deployed, the inflatable balloon is inflated and substantially surrounded by the expanded cage. The inflatable balloon may be deployed by a low pressure. The inflatable balloon may be deployed by an injection of a fluid supplied through the catheter assembly via a lumen provided in the catheter assembly to reach the inflatable balloon, which is typically done in inflating a conventional balloon. In one embodiment, the inflatable balloon is inflated sufficiently so that the outer surface of the inflated member is in contact with the inner surface of the expanded cage. In other embodiment, not all surface of the inflatable balloon contacts the cage. Alternatively yet, the inflatable balloon does not contact the inner surface of the cage and only needs to be deployed within the cage and proximate the lumen wall sufficiently to deliver the agent. The inflatable balloon may be separated from the lumen wall by the thickness of the struts in the cage. In one embodiment, the inflatable balloon is attached to the cage such that when the cage is expanded, the movement of the struts pull open the inflatable balloon. A space is thus created between the outer surface of the inflated balloon and vessel lumen wall. In one embodiment, the inflatable balloon, once inflated, reduces or substantially blocks blood flow across the inflatable balloon or down stream therefrom. In one embodiment, the catheter assembly is provided with perfusion paths to allow blood flows across the inflated inflatable balloon.

At 1008, an agent is delivered to the treatment site. In one embodiment, the agent is delivered to the space created between the outer surface of the inflated balloon and the vessel lumen wall. In one embodiment, the inflatable balloon is a microporous balloon adapted to carry the agent and once deployed, the agent is allowed to elute, exit the balloon, and reach the treatment site. The inflatable balloon may include ports placed peripherally around the inflatable balloon so as to allow the agent to exit the member and reach the treatment site. The ports may also be configured so that the exiting agent is directed or tend to travel in a preferred direction. For example, along a certain section of the inflatable balloon, the ports have a slanted or angled profile, and along other sections a straight profile to more efficiently distribute or deliver the agent to the treatment site. In one embodiment, the inflatable balloon includes one or more lumens reserved for carrying the agent or agents (the same or different) to be delivered to the treatment site. Typically, the agent is delivered to the treatment site within the space between the outer surface of the inflatable balloon and the lumen inner wall.

At 1010, optionally, after the agent is allowed to "bathe" the vessel wall at the treatment site, the inflatable balloon may be slightly inflated further to press or keep the agent at the delivered site for a duration of time. This further minimizes the drug washout effect typically seen in a conventional drug delivery system.

In one embodiment, a separate catheter device is used to inject an agent to the treatment site. In the present embodiment, the inflatable balloon needs not be porous so as to allow an agent to elute therefrom. Alternatively, in some treatment, an additional agent can be delivered via the injection method in addition to the porous inflatable balloon. This is particularly useful when multiple agents are to be delivered separately and to be mixed at the treatment site.

In one embodiment, the inflatable balloon is deflated and inflated intermittently, as the particular treatment or diagnostic circumstances dictate or require. For a certain treatment, a repeat treatment or dose application over certain time period is required. The inflatable balloon may be deflated (independently from the cage) so as to allow blood to flow through the vessel. The inflatable balloon is then inflated again for another treatment or another agent to be injected or delivered to the treatment site. Additionally, if desired, the inflatable balloon is repositioned to locally deliver the agent at an adjacent treatment site. In one embodiment, both the cage and the inflatable balloon are collapsed and moved to a different treatment site for another treatment. The cage is collapsed and withdrawn back into the delivery sheath by advancing the delivery sheath over the cage to fold the struts of the cage into a compressed state. The inflatable balloon can be deflated by a negative pressure or withdrawal of the fluid, or simply by the collapsing of the cage. The cage and the balloon can also be drawn proximally, while the delivery sheath is held stationary, into the delivery sheath to re-collapse themselves.

At 1012, once all deliver treatments are completed, the inflatable balloon and the cage are completely collapsed, and retrieved back into the delivery sheath and the catheter assembly is removed from the patient.

Although embodiments previously described focus mainly on a self-expanding cage, it is to be appreciated that the cage can otherwise be expanded by the inflatable balloon. It is to be understood that in such embodiment, the balloon is configured to be inflated using a low pressure and thereby expanding the cage with such low pressure so as to not impart unnecessary high force onto the vessel wall. In one embodiment, the cage is self-crimped instead of self-expandable. In other words the cage is naturally in a small diameter state and the balloon would have to push open the cage (with the low force, e.g., less than 2 atm) and the agent can then be delivered to the vessel wall similar to previously described. Upon completion of the agent delivery, the cage would collapse back to a small diameter. The present embodiment may eliminate the need for a delivery sheath previously described.

While the present invention is described herein in terms of certain preferred embodiments, those skilled in the art will recognize that various modifications and improvements may be made to the invention without departing from the scope thereof. For example, the catheters can be designed to have multiple frames (e.g., a bifurcated catheter), and a dilatation/stent delivery balloon can be added to the catheter proximal or distal to the frame to allow the catheter to perform the dual functions of agent delivery and balloon angioplasty/stent delivery. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An agent delivery assembly comprising:
    an inflatable balloon having an exterior working length between a distal section and a proximal section, wherein the inflatable balloon includes an uninflated state and a fully inflated state; and
    a self-crimping stent-like structure having a distal end and a proximal end, wherein the self-crimping stent-like structure includes an opened state and a small diameter state, wherein the self-crimping stent-like structure substantially covers the exterior working length of the inflatable balloon with the distal end being distal to the distal section and the proximal end being proximal to the proximal section, wherein the self-crimping stent-like structure is self-collapsible from the opened state when the inflatable balloon is in the fully inflated state to the small diameter state when the inflatable balloon is in the uninflated state and is removable from a lumen, wherein the self-crimping stent-like structure separates the inflatable balloon from a lumen wall when the inflatable balloon is in the fully inflated state within the lumen, and wherein the self-crimping stent-like structure does not damage a target tissue within the lumen when the self-crimping stent-like structure is in contact with the target tissue and the inflatable balloon is in the fully inflated state within the lumen.

2. The assembly of claim 1, wherein the self-crimping stent-like structure is expandable from the small diameter state when the inflatable balloon is in the uninflated state to the opened state when the inflatable balloon is in the fully inflated state.

3. The assembly of claim 2, wherein the inflatable balloon is configured to be fully inflated from the uninflated state to the fully inflated state with a pressure less than 2 atmospheres of pressure.

4. The assembly of claim 3 further comprising an attachment between the inflatable balloon and the self-crimping stent-like structure such that when the inflatable balloon is fully inflated, the self-crimping stent-like structure is pushed open to the opened state.

5. The assembly of claim 1, wherein the inflatable balloon includes openings to allow an agent to elute from inside the inflatable balloon toward the target tissue.

6. The assembly of claim 1 further comprising:
    a delivery sheath to constrain the self-crimping stent-like structure; and
    an inner member whereto the inflatable balloon and the self-crimping stent-like structure attach.

7. An agent delivery assembly comprising:
    an inflatable balloon having an exterior working length between a distal section and a proximal section, wherein the inflatable balloon includes an uninflated state and a fully inflated state, wherein the exterior working length of the inflatable balloon is tapered from the distal section toward the proximal section of the inflatable balloon when the inflatable balloon is in the fully inflated state, and wherein the distal section of the inflatable balloon is configured to seal off fluid flow past the distal section when the inflatable balloon is in the fully inflated state in a lumen; and
    a self-crimping stent-like structure having a distal end and a proximal end, wherein the self-crimping stent-like structure includes an opened state and a small diameter state, wherein the self-crimping stent-like structure substantially covers the exterior working length of the inflatable balloon with the distal end being distal to the distal section and the proximal end being proximal to the proximal section, wherein the self-crimping stent-like structure is self-collapsible from the opened state when the inflatable balloon is in the fully inflated state to the small diameter state when the inflatable balloon is in the uninflated state and is removable from the lumen, wherein the self-crimping stent-like structure separates the inflatable balloon from a lumen wall when the inflatable balloon is in the fully inflated state within the lumen, and wherein the self-crimping stent-like structure does not damage a target tissue within the lumen when the self-crimping stent-like structure is in contact with the target tissue and the inflatable balloon is in the fully inflated state within the lumen.

8. The assembly of claim 7, wherein the inflatable balloon is adapted to be independently inflated and capable of being intermittently inflated and deflated to open and close the self-crimping stent-like structure.

9. An agent delivery assembly comprising:
an inflatable balloon having a distal end, a proximal taper, and an exterior working length therebetween, wherein the inflatable balloon includes an uninflated state and a fully inflated state; and
a self-crimping stent-like structure having a distal end and a proximal end, wherein the self-crimping stent-like structure includes an opened state and a small diameter state, wherein the self-crimping stent-like structure substantially covers the proximal taper and the exterior working length, wherein the self-crimping stent-like structure is self-collapsible from the opened state when the inflatable balloon is in the fully inflated state to the small diameter state when the inflatable balloon is in the uninflated state and is removable from a lumen, wherein the self-crimping stent-like structure separates the inflatable balloon from a lumen wall when the inflatable balloon is in the fully inflated state within the lumen, and wherein the self-crimping stent-like structure does not damage a target tissue within the lumen when the self-crimping stent-like structure is in contact with the target tissue and the inflatable balloon is in the fully inflated state within the lumen.

\* \* \* \* \*